US00PP17481P3

(12) United States Plant Patent
Meilland

(10) Patent No.: US PP17,481 P3
(45) Date of Patent: Mar. 6, 2007

(54) MINIATURE ROSE PLANT NAMED 'MEIGENPI'

(50) Latin Name: *Rosa hybrida*
Varietal Denomination: Meigenpi

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 11/251,876

(22) Filed: Oct. 18, 2005

(65) Prior Publication Data

US 2006/0253944 P1 Nov. 9, 2006

(30) Foreign Application Priority Data

May 4, 2005 (FR) ..... PBR 19058

(51) Int. Cl.
*A01H 5/00* (2006.01)

(52) U.S. Cl. ..... Plt./116

(58) Field of Classification Search ..... Plt./116, Plt./118, 119

See application file for complete search history.

*Primary Examiner*—Kent Bell
*Assistant Examiner*—June Hwu
(74) *Attorney, Agent, or Firm*—Buchanan Ingersoll & Rooney PC

(57) ABSTRACT

A new and distinct variety of Miniature rose plant is provided which forms attractive bright yellow blossoms commonly with a margin of orange-red on the outer petals. When grown outside, more orange-red coloration commonly is displayed on the outer petals. The first blooming commonly occurs early in the season. A bushy growth habit is displayed. Very dense medium green semi-glossy foliage is formed. Good tolerance to diseases has been observed particularly with respect to Botrytis. The plant is well suited for pot forcing under greenhouse growing conditions to form a distinctive gift plant.

1 Drawing Sheet

Figures 1, 2, 3, 4, 5, 6, 7, 8, 9, 10, 11, 12, 13, 14, 15, 16, 17:
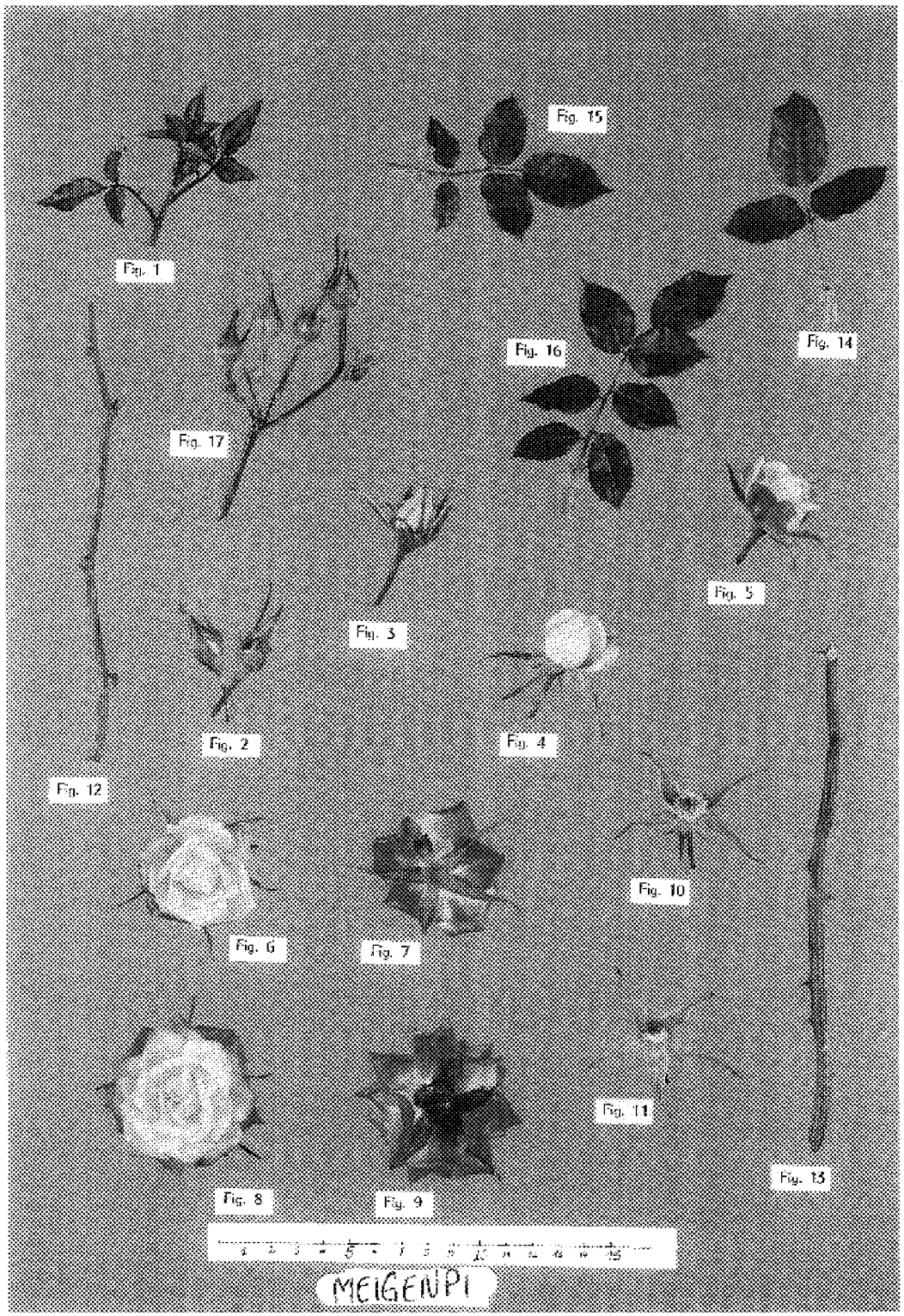

Botanical/commercial classification: *Rosa hybrida*/Miniature Rose Plant.
Varietal denomination: cv. Meigenpi.

SUMMARY OF THE INVENTION

The new variety of *Rosa hybrida* Miniature rose plant was created by artificial pollination wherein two parents were crossed which previously had been studied in the hope that they would contribute the desired characteristics. The female parent (i.e., the seed parent) of the new variety was the 'Meitomkin' variety (non-patented in the United States). The male parent (i.e., the pollen parent) was the product of the cross of the 'Savalife' variety (U.S. Plant Pat. No. 5,482) and the 'Meivoufal' variety (U.S. Plant patent application Ser. No. 10/844,340, filed May 13, 2004). The parentage of the new variety can be summarized as follows:

'Meitomkin'×('Savalife'×'Meivoufal').

The seeds resulting from the above pollination were sown and small plants were obtained which were physically and biologically different from each other. Selective study resulted in the identification of a single plant of the new variety.

It was found that the new variety of Miniature rose plant of the present invention possesses the following combination of characteristics:

(a) exhibits a bushy growth habit, (b) forms attractive bright yellow blossoms commonly with a margin of orange-red on the outer petals, (c) forms very dense medium green semi-glossy foliage, and (d) is well suited for pot forcing under greenhouse growing conditions.

The new variety well meets the needs of the horticultural industry. The first blooming commonly occurs early in the season. It is particularly well suited for pot forcing under greenhouse growing conditions to form a distinctive gift plant. It also can be grown to advantage outside, such as along walkways and in mixed border plantings. The bright yellow blossoms commonly initially display red undertones that transform to orange-red on the outer petal margins when opening. When grown outside, more orange-red coloration commonly is displayed on the petals.

The new variety has been found to undergo asexual propagation in France by a number of routes, including budding, grafting, and cuttage. Asexual propagation by the above-mentioned methods as performed in the South of France has shown that the characteristics of the new variety are strictly transmissible from one generation to another.

The new variety of the present invention can be readily distinguished from its ancestors. For instance, the 'Meitomkin' variety displays a considerably taller growth habit and the 'Savalife' variety forms smaller foliage. Also, the blossoms of the 'Meivoufal' are smaller and lack orange-red coloration at the margins of the outer petals.

The new variety of the present invention also can be readily distinguished from the 'Meiskaille' variety (U.S. Plant Pat. No. 14,274) and the 'Meitoleil' variety (non-patented in the United States). More specifically, the 'Meiskaille' variety forms larger blossoms which bear no orange-red coloration at the margins of the petals, and the 'Meitoleil' variety likewise forms blossoms which lack orange-red coloration on the petal margins.

The new variety has been named 'Meigenpi', and is being marketed under the RAINBOW SUNBLAZE trademark.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were one year of age and were observed during September while growing on *Rosa froebelii* rootstock in greenhouses at LeCannet des Maures, Var, France. Dimensions in centimeters are shown at the bottom of the photograph.

FIG. 1—illustrates a specimen of a young shoot;

FIG. 2—illustrates specimens of two floral buds before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower during the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets —plan view—upper surface;

FIG. 15—illustrates a specimen of a leaf with five leaflets—plan view—upper surface;

FIG. 16—illustrates a specimen of a leaf with seven leaflets—plan view—upper surface; and FIG. 17—illustrates a cluster of buds.

DETAILED DESCRIPTION

The chart used in the identification of the colors is that of The Royal Horticultural Society (R.H.S. Colour Chart). The description is based on the observation of one year-old specimens of the new variety which were observed during September while growing on their own roots in greenhouses at LeCannet des Maures, Var, France.

Class: Miniature.

Plant:

*Height.*—Approximately 25 to 30 cm on average at the end of the growing season.

*Width.*—Approximately 25 cm on average at the end of the growing season.

*Habit.*—Bushy.

Branches:

*Color.*—Young stems: near Yellow-Green Group 144A. Adult wood: near Yellow-Green Group 146C.

*Texture.*—Young stems: smooth with some thorns. Adult wood: smooth with some thorns.

*Thorns.*—Size and quantity: on young stems, approximately 4 on average having a length of approximately 0.4 cm over a stem length of 10 cm, and on adult stems approximately 6 on average having a length of approximately 0.5 cm over a stem length of 10 cm. Color: on young stems, near Yellow-Green Group 145C, and on adult near Yellow-Green Group 146D. Configuration: rather straight and very longish, pointed on the upper surface, slightly concave on the under surface, and narrow at the base.

Leaves:

*Size.*—A seven-leaflet leaf commonly is approximately 7.3 cm in length on average, and approximately 4.5 cm in width on average.

*Petioles.*—Upper surface: pubescent, non-glandular, and near Green Group 137B on the upper surface. Under surface: bear a very few prickles and near Yellow-Green Group 144A in coloration. Size: approximately 2 cm in length on the terminal leaflet.

*Stipules.*—Adnate, pectinate, rather broad, smooth, approximately 1.4 cm in length on average, approximately 0.5 cm in width on average, near Yellow-Green Group 144B on the upper surface, and near Yellow-Green Group 144A on the under surface.

*Leaflets.*—Number: 3, 5, and 7 (most often). Shape: with a pointed tip and an obtuse base (as illustrated). Texture: rather thick. Serration: small and single. General appearance: very dense, medium green and semi-glossy. Size: terminal leaflets commonly measure approximately 3.5 cm in length on average and approximately 2.7 cm in width on average. Color (young foliage): Upper surface: near Green Group 137B. Under surface: near Green Group 138B. Color (mature foliage): Upper surface: near Green Group 137C. Under surface: near Green Group 138B.

Inflorescence:

*Number of flowers.*—Commonly approximately 1 to 5 flowers per stem, commonly in clusters.

*Peduncle.*—Smooth, firm, near Green Group 138B in coloration, approximately 2.5 cm in length on average, and approximately 0.2 cm in diameter on average.

*Sepals.*—Upper surface: smooth, and near Green Group 138B and 138C in coloration. Under surface: smooth, and near Green Group 138B in coloration. Shape: narrow, longish-pointed at the tip, incurved at the base, and bear some weak foliaceous extensions. Length: approximately 2.7 to 3 cm on average. Width: approximately 0.6 cm on average.

*Buds.*—Shape: conical. Size: approximately 1.8 cm in length on average, and approximately 1.5 cm in width on average. Color: as the calyx breaks on the upper surface, near Yellow Group 13A slightly margined with Orange-Red Group 33B on the external petals and near Yellow Group 13A on the inner petals, and on the under surface near Yellow Group 13B on the external petals and the inner petals.

*Flower.*—Form: double and flat cup-shaped. Diameter: approximately 5 to 6 cm on average when fully open. Color (when opening begins): Upper surface: near Yellow Group 13A and widely margined with Orange-Red Group 33B on the external petals, and near Yellow Group 13A on the inner petals. Under surface: near Yellow-Group 13A and slightly margined with Orange-Red Group 33B on the external petals, and near Yellow Group 13A on the inner petals. Color (when blooming): Upper surface: near Yellow Group 13B and 13C and widely margined with Red Group 55B and Orange-Red Group 33B on the external petals, and near Yellow Group 13B and 13C on the inner petals. Under surface: near Yellow Group 13B and 13C and slightly margined and suffused with Red Group 55B and Orange-Red Group 33B on the external petals, and near Yellow Group 13B and 13C on the inner petals. Basal petal spot: none observed. Discoloration: very slight with age. Fragrance: none. Anthers: near Yellow-Group 9A in coloration, regularly arranged around the styles, and approximately 0.1 cm in size on average. Stamen number: approximately 39 on average. Filaments: near Yellow Group 9D in coloration, and approximately 0.2 cm in length on average. Pollen: present and near Yellow Group 9A in coloration. Pistil number: approximately 70 on average. Stigmas: near Red Group 54C in coloration, and approximately 0.1 cm in size on average. Styles: near Yellow-Green Group 150D in coloration, and approximately 0.2 cm in length. Petal number: approximately 57 to 70 on average under normal growing conditions. Petal arrangement: imbricated. Petal shape: possess an obtuse base and a reflexed tip. Petal size: approximately 1.6 to 1.9 cm in length on average, and approximately 1.5 cm in width on average. Petal texture: smooth and firm. Petal drop: good, the petals commonly detach cleanly before drying. Petaloids: none observed. Receptacle: near Green Group 138B in coloration, funnel-shaped in cross section, and approximately 0.7 cm in length and width. Hips: none observed. Lasting quality: approximately three weeks on the plant on average, and approximately 12 days on average when cut and placed in a vase.

Development:

*Vegetation.*—Strong.

*Blooming.*—Abundant.

*Tolerance to diseases.*—Good, especially with respect to Botrytis.

*Tolerance to cold.*—Has withstood −10° C. during observations to date, and grows well in U.S.D.A. Hardiness Zone 7A.

*Tolerance to heat.*—Has withstood 35° C. during observations to date.

*Aptitude to bear fruit.*—None.

*Aptitude to forcing.*—Excellent.

I claim:

1. A new and distinct variety of Miniature rose plant characterized by the following combination of characteristics:

(a) exhibits a bushy growth habit, (b) forms attractive bright yellow blossoms commonly with a margin of orange-red on the outer petals, (c) forms very dense medium green semi-glossy foliage, and (d) is well suited for pot forcing under greenhouse growing conditions;

substantially as herein shown and described.

* * * * *

MEIGENPI